United States Patent

Vorbrüggen et al.

[11] 4,219,479
[45] Aug. 26, 1980

[54] 5-CYANO-PROSTACYCLIN DERIVATIVES

[75] Inventors: Helmut Vorbrüggen; Werner Skuballa; Bernd Radüchel; Wolfgang Losert; Olaf Loge, all of Berlin; Bernd Müller, Aachen; Gerda Mannesmann, Berlin, all of Fed. Rep. of Germany

[73] Assignee: Schering Aktiengesellschaft, Berlin and Bergkamen, Fed. Rep. of Germany

[21] Appl. No.: 963,240

[22] Filed: Nov. 24, 1978

[30] Foreign Application Priority Data

Nov. 25, 1977 [DE] Fed. Rep. of Germany ....... 2753244

[51] Int. Cl.$^2$ .................. A61K 31/335; C07D 307/93
[52] U.S. Cl. .................................... 424/263; 424/274; 424/275; 424/283; 424/285; 542/426; 542/429; 542/430; 546/269; 549/60; 260/326.36; 260/345.7 P; 260/345.8 P; 260/346.22; 260/346.73
[58] Field of Search ...................... 260/346.22, 346.73, 260/326.36, 345.7 P, 345.8 P; 546/269; 542/426, 429, 430; 424/263, 274, 275, 283, 285; 549/60

[56] References Cited

PUBLICATIONS

Vorbrüggen, Tetrahedron Letters, 1968, pp. 1631–1633.

Primary Examiner—Henry R. Jiles
Assistant Examiner—Bernard Dentz
Attorney, Agent, or Firm—Millen & White

[57] ABSTRACT

Stabilized prostacyclins having a wide range of pharmacological activity and long duration of such activity, have the formula

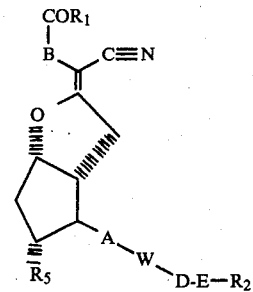

wherein
$R_1$ is (a) $OR_3$, wherein $R_3$ is hydrogen, alkyl, cycloalkyl, aryl or a heterocyclic residue; or (b) $NHR_4$ wherein $R_4$ is an acid residue;
B is straight-chain or branched alkylene of 2–10 carbon atoms;
A is —CH$_2$—CH$_2$—, cis—CH=CH—, trans—CH=CH— or —C≡C—,
W is free or functionally modified hydroxymethylene or free or functionally modified

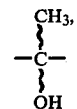

wherein the OH-group can be in the α- or β-position;
D and E together are a direct bond; or
D is straight-chain or branched alkylene of 1–5 carbon atoms; and
E is oxygen or sulfur or a direct bond,
$R_2$ is alkyl, cycloalkyl, optionally substituted aryl or a heterocyclic group; and
$R_5$ is free or functionally modified hydroxy; and when $R_3$ is hydrogen, the salts thereof with physiologically compatible bases.

27 Claims, No Drawings

5-CYANO-PROSTACYCLIN DERIVATIVES

BACKGROUND OF THE INVENTION

The present invention relates to novel prostacylin derivatives, processes for the preparation thereof and their use as medicinal agents.

It has been known from various, recently published works (Nature [London] 263, 663 [1976]; Prostaglandins 14, 210 [1977]) that prostaglandin $I_2$ ($PGI_2$) inhibits ADP-induced blood platelet aggregation. In addition, $PGI_2$ has a blood-pressure-lowering effect due to its dilating action on the smooth musculature of arteries.

However, $PGI_2$ does not possess the stability necessary for a medicinal agent. Thus, the half-life of $PGI_2$ is only a few minutes at physiological pH values and at room temperature.

SUMMARY OF THE INVENTION

Accordingly, it is an object of this invention to provide novel prostacyclins having high stability, and also wide spectra of activity and long duration of activity.

Upon further study of the specification and appended claims, further objects and advantages of this invention will become apparent to those skilled in the art.

These objects have been achieved by providing prostane derivatives of the formula I

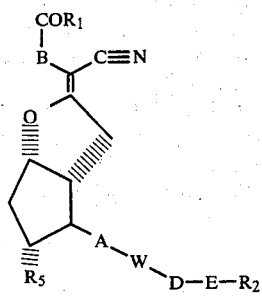

I, wherein $R_1$ is (a) $OR_3$, wherein $R_3$ is hydrogen, alkyl, cycloalkyl, aryl or a heterocyclic residue; or (b) $NHR_4$ wherein $R_4$ is an acid residue;

B is straight-chain or branched alkylene of 2–10 carbon atoms;

A is —$CH_2$—$CH_2$—, cis—CH=CH—, trans—CH=CH— or —C≡C—,

W is free or functionally modified hydroxymethylene or free or functionally modified

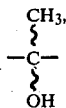

wherein the OH-group can be in the α-or β-position;

D and E together are a direct bond; or

D is straight-chain or branched alkylene of 1–5 carbon atoms; and

E is oxygen or sulfur or a direct bond, $R_2$ is alkyl, cycloalkyl, optionally substituted aryl or a heterocyclic group; and $R_5$ is free or functionally modified hydroxy; and when $R_3$ is hydrogen, the salts thereof with physiologically compatible bases.

DETAILED DISCUSSION

It has now been found that the introduction of a nitrile group at its enol ether double bond stabilizes a prostacyclin. At the same time, the pharmacological spectrum of its activity is preserved and the duration of effectiveness is markedly extended.

In formula I, suitable alkyl groups $R_3$ include straight-chain or branched alkyl groups. Typically, they have 1–10 carbon atoms, such as, for example, methyl, ethyl, propyl, butyl, isobutyl, tert-butyl, pentyl, neopentyl, heptyl, hexyl, decyl, and the like.

In addition to alkyl groups having greater than 10 carbon atoms, other substantial equivalents of the $C_{1-10}$ alkyl groups include the $R_3$ alkyl groups which are substituted by halogen atoms, $C_{1-4}$ alkoxy groups, optionally substituted $C_{6-10}$ aryl groups, (whose substituents may be chosen from those described for the $R_3$ aryl groups below), $diC_{1-4}$ alkylamino groups, and $triC_{1-4}$ alkyl ammonium groups. Preferred are those alkyl groups which are monosubstituted. Examples of such $R_3$ alkyl substituents include flourine, chlorine, or bromine atoms, phenyl, dimethylene, diethylamine, methoxy, ethoxy, etc. Preferred $R_3$ alkyl groups are those of 1–4 carbon atoms, such as, for example, methyl, ethyl, propyl, dimethylaminopropyl, isobutyl and butyl.

Suitable aryl groups $R_3$ include substituted as well as unsubstituted $C_{6-10}$ aryl groups, such as, for example, phenyl, 1-naphthyl and 2-naphthyl. These can be substituted by 1–3 halogen atoms, a phenyl group, 1–3 alkyl groups each of 1–4 carbon atoms or a chloromethyl, fluoromethyl, trifluoromethyl, carboxy, hydroxy or $C_{1-4}$ alkoxy group. Substituents in the 3- and 4-positions of the phenyl ring are preferred, for example, fluorine, chlorine, alkoxy, or trifluoromethyl. In the 4-position, substitution by hydroxy is preferred.

Suitable cycloalkyl groups $R_3$ include those of 4–10, preferably 5 and 6 carbon atoms in the ring. The ring can be substituted by alkyl groups of 1–4 carbon atoms, i.e., there can be a total of 4–14 carbon atoms in the cycloalkyl group. Examples include cyclopentyl, cyclohexyl, methylcyclohexyl, and adamantyl.

Suitable heterocycles include 5 and 6 membered aromatic monocycles containing one S, N or O ring atom. Substantially equivalent $R_3$ heterocyclic groups include 5- and 6-membered heterocycles containing at least one hetero atom, preferably nitrogen, oxygen or sulfur. Examples include 2-furyl, 2-thienyl, 2-pyridyl, 3-pyridyl, 4-pyridyl and others.

Physiologically compatible acid residues are suitable as the acid residue $R_4$. The acid residue typically is an acyl group of the acid. Preferred acids are organic carboxylic acids and sulfonic acids of 1–15 carbon atoms of the aliphatic, cycloaliphatic, aromatic, aromatic-aliphatic and heterocyclic series. These acids can be saturated or unsaturated, and/or polybasic and/or substituted in conventional fashion. Examples of such substituents are alkyl, hydroxy, alkoxy, oxo, amino and halogen. Hydrocarbon carboxylic and sulfonic acids of 1–15 carbon atoms form the basic group of such acids.

Suitable carboxylic acids include, for example: formic acid, acetic acid, propionic acid, butyric acid, isobutyric acid, valeric acid, isovaleric acid, caproic acid, enanthic acid, caprylic acid, pelargonic acid, capric acid, undecyclic acid, lauric acid, tridecyclic acid, myristic acid, pentadecyclic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid. Especially preferred acyl residues are those of up to 10 carbon atoms.

Suitable sulfonic acids include, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid and pyrrolidino-, piperidino-, piperazino-, N-methylpiperazino-, and morpholinosulfonic acids.

As is evident from the diverse nature of the illustrative carboxylic and sulfonic acids named above, the exact structure of the acid residue is not critical. Therefore, contemplated substantial equivalents of the preferred hydrocarbon carboxylic and sulfonic acids are those other types of acids named above, e.g., the heterocyclic acids and the substituted acids, etc., as well as conventional acids whose acyl groups are in vivo hydrolyzable and pysiologically acceptable.

The hydroxy groups of $R_5$ and those of W can be functionally modified, for example, by etherification or esterification. The free or modified hydroxy groups in W can be in the α- or β-position; free hydroxy groups being preferred.

Suitable such ether and acyl residues are well known to persons skilled in the prostaglandin art and are in vivo hydrolyzable and physiologically acceptable. (See, e.g., as disclosed in Mc.Omie Ed., Protective Groups in Organic Chemistry, Plenum Press, N.Y. 1973.) Preferred are ether residues which can be readily split-off, such as, for example, tetrahydropyranyl, tetrahydrofuranyl, α-ethoxyethyl, trimethylsilyl, dimethyl-tert-butylsilyl and tribenzylsilyl. Suitable acyl residues are the same as those mentioned above for $R_4$. Examples include acetyl, propionyl, butyryl and benzoyl.

Suitable $R_2$ aliphatic groups include straight-chain and branched alkyl, alkenyl and alkynyl groups, preferably saturated ons, i.e., alkyl, all of 1–10, especially 1–6 carbon atoms. Substantially equivalent groups are the same groups which are substituted by aryl (e.g., those mentioned above for $R_3$), which latter can also be substituted, if desired (e.g., by the substituents mentioned above for the $R_3$ aryl groups). Suitable such $R_2$ groups include methyl, ethyl, propyl, butyl, isobutyl, tert-butyl, pentyl, hexyl, heptyl, octyl, butenyl, isobutenyl, propenyl, pentenyl, benzyl and p-chlorobenzyl.

Suitable cycloalkyl $R_2$ groups may contain 4–10, preferably 5 and 6 carbon atoms in the ring. The rings can be substituted by alkyl groups of 1–4 carbon atoms, i.e., the total number of carbon atoms can be 4–14 for the overall cycloalkyl group. Examples are cyclopentyl, cyclohexyl, methylcyclohexyl and adamantyl.

Suitable $R_2$ $C_{6-10}$ aryl groups include phenyl, 1-naphthyl and 2-naphthyl. Substantial equivalents thereof include the aryl groups substituted by 1–3 halogen atoms, phenyl, 1–3 alkyl groups each of 1–4 carbon atoms or a chloromethyl, fluoromethyl, trifluoromethyl, carboxy, $C_{1-4}$ alkoxy or hydroxy group. Substitution in the 3- and 4-positions on the phenyl ring is preferred, for example, by fluorine, chlorine, alkoxy, or trifluoromethyl; in the 4-position substitution by hydroxy is preferred.

Suitable heterocycles include 5- and 6-membered aromatic monocycles containing one S, N or O ring atom. Substantially equivalent $R_2$ heterocyclic groups include 5- and 6 membered heterocycles containing at least one hetero atom, preferably nitrogen, oxygen or sulfur. Examples include 2-furyl, 2-thienyl, 2-pyridyl, 3-pyridyl, 4-pyridyl, etc.

Suitable alkylene groups B include straight-chain or branched alkylene residues. Substantial equivalents of such groups are unsaturated alkylene groups. However, saturated alkylene residues are preferred, especially of 1–10, most especially of 1–5 carbon atoms. Examples include methylene, ethylene, 1,2-propylene, ethylethylene, trimethylene, tetramethylene, pentamethylene, hexamethylene, etc.

Suitable physiologically acceptable salts are those derived from inorganic and organic bases. These are conventionally employed with prostaglandins and are known to persons skilled in the art for the production of physiologically compatible salts. Examples are alkali hydroxides, such as sodium and potassium hydroxide, alkaline earth hydroxides, such as calcium hydroxide, ammonia, and amines, such as ethanolamine, diethanolamine, triethanolamine, N-methylglucamine, morpholine, tris(hydroxymethyl)methylamine, etc.

The present invention furthermore relates to a process for the preparation of the prostane derivatives of Formula I which comprises reacting, in a manner known per se (as described by H. Vorbrueggen in Tetrahedron Letters 1968, 1631) a compound of Formula II

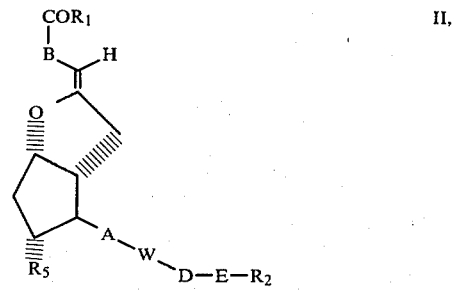

wherein $R_1$, $R_2$, $R_3$, $R_5$, A, B, W, D, and E are as defined above, optionally after blocking any free hydroxy groups present, with a sulfonyl isocyanate of Formula III $R_6SO_2NCO$            III wherein $R_6$ is phenyl optionally substituted by alkyl of 1–4 carbon atoms, halogenated alkyl or halogen; and then reacting the resultant product with a tertiary amine or a tertiary amide.

It is subsequently possible, if desired, in the thus-obtained products, in any desired sequence, conventionally, to liberate blocked hydroxy groups, and/or to esterify or etherify free hydroxy groups, to saponify an esterified carboxy group or to esterify a carboxy group;

and/or to react a carboxy group with compounds of Formula IV

IV wherein $R_4$ is as defined above; and/or to convert a carboxy group into a salt with a physiologically compatible base.

The reaction of the enol ethers II to the compounds of Formula I takes place, in succession in the same reaction vessel, i.e., in situ, with sulfonyl isocyanates of Formula III; and with a tertiary amine in an inert solvent, preferably tetrahydrofuran, dioxane, diethyl ether, toluene, or a tertiary amide, preferably without a solvent. Among the sulfonyl isocyanates of Formula III are included benzenesulfonyl isocyanate, p-toluenesulfonyl isocyanate, as well as the halo sulfonyl isocyanates of the halogens, fluorine, chlorine, and bromine. Especially preferred for the reaction of the compounds of Formula II is chlorosulfonyl isocyanate.

The reaction with the sulfonyl isocyanates of Formula III takes place at temperatures of between 30° C. and −100° C., preferably between −70° C. and 0° C. The reaction with a tertiary amine or a tertiary amide takes place at temperatures of between −100° C. and 30° C., preferably between −70° C. and +30° C. Suitable tertiary amines are, for example: triethylamine, trimethylamine, dimethylisopropylamine, dimethylisopropylamine. DBN (1,5-diazabicyclo [4,3,0]nonene-5), DBU (1,5-diazabicyclo[5,4,0]undecene-5, etc. are also useful. A preferred tertiary amide is dimethylformamide.

The saponification of the prostaglandin esters is conducted according to the methods known to those skilled in the art, e.g., with basic catalysts.

The introduction of the ester group —$OR_3$ for $R_1$ wherein $R_3$ is an alkyl group of 1–10 carbon atoms also takes place according to methods known to persons skilled in the art. The carboxy compounds can be reacted, for example, conventionally with diazo hydrocarbons. The esterification with diazo hydrocarbon can be performed, for example, by mixing a solution of the diazo hydrocabon in an inert solvent, preferably in diethyl ether, with the carboxy compound in the same or in another inert solvent, e.g., methylene chloride. After the reaction has been terminated within 1–30 minutes, the solvent is removed, and the ester is purified as usual. The required diazoalkanes are either known or they can be prepared according to conventional methods [Org. Reactions, 8: 389–394 (1954)].

The introduction of the ester group —$OR_3$ for $R_1$ wherein $R_3$ is a substituted or unsubstituted aryl group also takes place according to methods known to persons skilled in the art. For example, the carboxy compounds can be reacted with the corresponding aryl hydroxy compounds with the use of dicyclohexylcarbodiimide in the presence of a suitable base, for example, pyridine or triethylamine, in an inert solvent. Suitable solvents include methylene chloride, ethylene chloride, chloroform, ethyl acetate and tetrahydrofuran; preferably chloroform. The reaction is conducted at temperatures of between −30° C. and +50° C., preferably at +10° C. For compounds wherein $R_3$ is cycloalkyl, the foregoing procedure described for the $R_3$ alkyl-containing compounds may be analogously employed. For all the compounds wherein $R_3$ is an aromatic heterocycle, the foregoing procedure described for the $R_3$ aryl-containing compounds may analogously be employed.

The prostaglandin derivatives of Formula I wherein $R_1$ is hydroxy can be converted to salts with suitable amounts of the corresponding inorganic bases by conventional neutralization techniques. For example, when dissolving the corresponding PG acids in water containing the stoichiometric quantity of the base, the solid inorganic salt can be obtained after evaporation of the water or after adding a water-miscible solvent, e.g., alcohol or acetone.

For example, in order to produce an amine salt by the conventional process, the PG acid is dissolved in a suitable solvent, for example, ethanol, acetone, diethyl ether, or benzene, and at least the stoichiometric amount of the amine is added to this solution. In this case, the salt is ordinarily obtained in the solid phase or is isolated in the usual way after evaporation of the solvent.

The functional modification of the free OH-groups also takes place according to methods known to those skilled in the art. To introduce the ether blocking groups, for example, the reaction can be carried out with dihydropyran in methylene chloride or chloroform with the use of an acidic condensation agent, for example, p-toluenesulfonic acid. The dihydropyran is utilized in excess, preferably 4–10 times the amount of the theoretical quantity required. The reaction is normally terminated at 0° C. to 30° C. after 15–30 minutes.

The acyl blocking groups are introduced by conventionally reacting a compound of Formula I with the necessary carboxylic acid derivative, e.g., an acid chloride, an acid anhydride, or the like.

The liberation of a functionally modified OH-group in the compounds of Formula I also takes place according to known methods. For example, the ether blocking groups can be split off in an aqueous solution of an organic acid, e.g., acetic acid, propionic acid, etc., or in an aqueous solution of an inorganic acid, e.g., hydrochloric acid. To improve the solubility, a water-miscible inert organic solvent can be suitably added. Suitable such organic solvents include, for example, alcohols, such as methanol and ethanol, and ethers, such as dimethoxyethane, dioxane, and tetrahydrofuran. Tetrahydrofuran is preferably employed. The splitting-off step is preferably conducted at temperatures of between 20° C. and 80° C.

The splitting-off of silyl ether blocking groups can be performed, for example, with tetrabutylammonium fluoride. Suitable solvents include, for instance, tetrahydrofuran, diethyl ether, dioxane, methylene chloride, etc. The splitting-off step is effected preferably at temperatures of between 0° C. and 80° C.

The saponification of the acyl groups can be performed conventionally, for example, with alkali or alkaline earth carbonates or hydroxides in an alcohol or in an aqueous solution of an alcohol. Alcohols which can be used are aliphatic alcohols, e.g., methanol, ethanol, butanol, etc., preferably methanol. Examples of alkali carbonates and hydroxides are potassium and sodium salts, but the potassium salts are preferred. Examples of suitable alkaline earth carbonates and hydroxides are calcium carbonate, calcium hydroxide, and barium carbonate. The reaction takes place at −10° C. to 70° C., preferably at 25° C.

The reaction of the compounds of Formula I wherein $R_3$ is hydrogen with an isocyanate of Formula IV takes place optionally with the addition of a tertiary amine, e.g., triethylamine or pyridine. The reaction can be effected either without a solvent or in an inert solvent, preferably acetonitrile, tetrahydrofuran, acetone, dimethylacetamide, methylene chloride, diethyl ether, benzene, toluene or dimethyl sulfoxide, at temperatures of above or below room temperature, e.g., between −80° C. and 100° C., preferably at 0°–30° C.

If the starting compound contains OH-groups in the prostane residue, these OH-groups are also reacted. If final products which contain free hydroxy groups in the prostane residue are desired in the last stage of the process, then, advantageously, starting compounds should be employed wherein these free hydroxy groups are intermediarily protected by ether or acyl residues which are preferably readily split off.

The compounds of Formula II serving as starting materials can be produced, for example, by conventionally reacting a known prostaglandin F derivative of Formula V

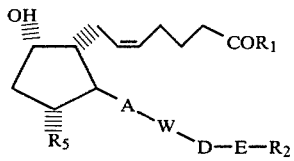

with iodine in the presence of an alkali hydrogen carbonate or alkali carbonate to the compounds of Formula VI

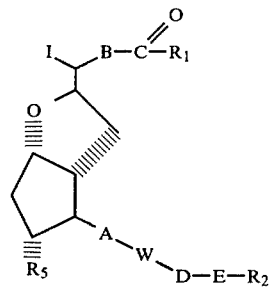

The various substituents in Formulae V and VI are as defined above. (R. A. Johnson et al. JACS 99, 4182 (1977))

Subsequently, free hydroxy groups can be optionally blocked by esterification or silylation. Depending on the desired A or $R_1$ groups in the final products of Formula I, it is possible, if desired, to hydrogenate double bonds in VI or, if desired, to esterify a carboxy group, or to react a carboxy group with compounds of Formula IV.

The reaction of the compounds of Formula VI to the compounds of Formula II can be conducted, for example, with 1,5-diazabicyclo[4,3,0]nonene-5 (DBN) or with 1,5-diazabicyclo[5,4,0]undecene-5 (DBU) in an inert solvent, such as benzene, toluene, tetrahydrofuran, etc., or with sodium methylate in methanol. The splitting-off of the hydrogen halide takes place at temperatures of between 0° C. and 120° C., preferably at 20°–60° C. (N. Whittaker Tetrahedron Letters 1977, 2805)

The compounds of this invention have a blood-pressure-lowering effect. Furthermore, these compounds are suitable for the inhibition of thrombocyte aggregation.

The novel prostacyclin derivatives of Formula I, thus, are valuable pharmaceuticals. This is moreover true since they are distinguished over corresponding prostaglandins by an improved specificity and, above all, by a considerably longer period of effectiveness, while exhibiting a similar spectrum of activity. As compared to PGE, PGA, and PGI compounds, the novel prostaglandins are distinguished by higher stability. The good tissue specificity of the novel prostaglandins is demonstrated in the investigation on smooth-muscular organs, such as, for example, on the guinea pig ileum or on the isolated rabbit trachea, where a substantially lower stimulation can be observed than when applying natural prostaglandins.

The novel prostaglandin analogs possess the pharmacological properties typical for prostaglandins, such as, for example, lowering of the blood pressure, inhibition of thrombocyte aggregation, inhibition of gastric acid secretion, etc. They, of course, can be administered to mammals, including humans.

Upon intravenous injection on awake, hypertonic rats in doses of 20 and 100 μg/kg of body weight, the compounds of this invention show a stronger blood-pressure-lowering effect than $PGE_2$ and $PGA_2$ compounds without triggering at these doses diarrhea, as would $PGE_2$, or cardiac arrhythmias, as would $PGA_2$.

Upon intravenous injection on narcotized rabbits, the compounds of this invention, as compared to $PGE_2$ and $PGA_2$ compounds, show a stronger and considerably longer lasting lowering of the blood pressure, without affecting other smooth-muscular organs or organ functions.

The administration of the claimed compounds for each of the foregoing uses is analogous to that for conventional prostglandin-type compounds employed for each utility. For example, for lowering of the blood pressure, 5–1000 mg/kg/day of each compound may be administered analogously to the administration of the conventional prostaglandins $PGE_2$ and $PGA_2$.

| | Utility | Dosage (mg/kg/day) | Analogous compound for Administration |
|---|---|---|---|
| (a) | inhibition of thrombocyte aggregation | 5–1000, preferable 20–250 | $PGE_1$ |
| (b) | inhibition of gastric acid secretion | 5–1000, preferable 20–250 | $PGE_2$ |

Typically, the unit dosage form is 20–250 mg in a conventional carrier.

The pharmacologically active compounds of Formula I can be processed in accordance with conventional methods of galenic pharmacy to product medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, which are sterile and injectable, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-Cyanoprostacyclin Methyl Ester 11,15-Diacetate

At $-70°$ C., 3.55 ml. of a chlorosulfonyl isocyanate solution (production: 2.3 ml. of chlorosulfonyl isocyanate is dissolved in 50 ml. of absolute ether) is added dropwise to a solution of 320 mg. of prostacyclin methyl ester 11,15-diacetate in 4.2 ml. of absolute ether. The mixture is gradually heated to 0° C. and then 3.55 ml. of a solution of triethylamine (production: 100.2 mg. of triethylamine is dissolved in 5 ml. of methylene chloride) is added dropwise thereto. The mixture is agitated for 1 hour at 0° C., for 15 minutes at 20° C., then poured on a mixture of sodium bicarbonate solution and ice water, extracted three times with ether, the organic extract is shaken twice with brine, dried over magnesium sulfate, and evaporated under vacuum. Purification by preparative thin-layer chromatography (PTLC) (silica gel, ether) yields 60 mg. of the title compound as a colorless oil.

IR (CHCl$_3$): 2959, 2930, 2860, 2203, 1730, 1650, 1372, 1245, 970 cm$^{-1}$.

The starting material for the title compound was produced as follows:

1(a) 5,6-Dihydro-5-iodoprostacyclin Methyl Ester

Under agitation at 0° C., 65.2 ml. of a 2.5% ethereal iodine solution is added dropwise within 3 hours to a mixture of 2.16 g. of prostaglandin F$_{2\alpha}$ methyl ester, 5.40 g. of sodium bicarbonate, 50 ml. of ether, and 90 ml. of water. After 22 hours at 0° C., the mixture is diluted with ether, shaken with dilute sodium thiosulfate solution, washed with water until neutral, dried over magnesium sulfate, and evaporated under vacuum. Filtration over silica gel with ether/ethyl acetate (1+1) yields 2.81 g. of the title compound as a colorless oil.

IR (CHCl$_3$): 3600, 3400, 2932, 1730, 975 cm$^{-1}$.

1(b) 5,6-Dihydro-5-iodoprostacyclin Methyl Ester 11,15-Diacetate 400 mg. of the diol produced according to Example 1(a) is dissolved in 0.8 ml. of acetic anhydride and 3 ml. of pyridine and is allowed to stand for 18 hours at room temperature. After evaporation under vacuum, 467 mg. of the diacetate is obtained as a colorless oil, which is uniform as determined by TLC.

IR (CHCl$_3$): 2958, 2948, 2860, 1732, 1372, 1245, 976 cm$^{-1}$.

1(c) Prostacyclin Methyl Ester 11,15-Diacetate

A solution of 200 mg. of the diacetate prepared according to 1(b) in 2 ml. of benzene is combined with 1 ml. of 1,5-diazabicyclo[4,3,0]non-5-ene (DBN) and agitated for 20 hours under argon at 40° C. The mixture is diluted with ether, shaken three times with ice water, dried over sodium sulfate, and concentrated under vacuum at 20° C., thus obtaining the oily title compound which is used without further purification.

EXAMPLE 2

5-Cyanoprostacyclin Methyl Ester 250 mg. of the compound prepared according to Example 1, 150 m. of potassium carbonate, and 10 ml. of methanol are agitated for 3.5 hours at room temperature under argon. The mixture is then diluted with ether, washed neutral with water, dried over MgSO$_4$, and evaporated under vacuum at 25° C.

IR (CHCl$_3$): 3600, 3430, 2937, 2860, 2212, 1730, 1650, 972 cm$^{-1}$.

EXAMPLE 3

5-Cyanoprostacyclin

A solution of 25 mg. of the compound produced in accordance with Example 2 in 1.5 ml. of methanol is combined with 0.25 ml. of 1N sodium hydroxide solution and agitated for 4 hours at 25° C. under argon. Thereafter, the mixture is concentrated under vacuum, taken up in 3 ml. of brine, and the solution is adjusted to pH 7 with 0.5% citric acid. The reaction mixture is extracted four times with methylene chloride, the organic extract is shaken once with brine, dried over magnesium sulfate, and evaporated under vacuum, thus obtaining 22 mg. of the title compound as an oil, uniform as determined by TLC; this oil crystallizes when stored at $-20°$ C.

IR (CHCl$_3$): 3600, 2930, 2862, 2211, 1710, 1650, 973 cm$^{-1}$.

EXAMPLE 4

5-Cyano-15-methylprostacyclin Methyl Ester 11,15-Diacetate

At $-70°$ C. 7.2 ml. of a chlorosulfonyl isocyanate solution (production: 2.3 ml. of chlorosulfonyl isocyanate is dissolved in 50 ml. of absolute ether) is added dropwise to a solution of 644 mg. of 15-methylprostacyclin methyl ester 11,15-diacetate in 9 ml. of absolute ether; the mixture is gradually heated to 0° C. and then 7.2 ml. of a solution of triethylamine (production: 200 mg. of triethylamine is dissolved in 10 ml. of methylene chloride) is added dropwise thereto. The mixture is stirred for 1 hour at 0° C., for 15 minutes at 20° C., and then poured on ice-cold sodium bicarbonate solution. The reaction mixture is extracted three times with ether, the organic extract is shaken twice with brine, dried over magnesium sulfate, and evaporated under vacuum. After purification by PTLC (ether), 135 mg. of the title compound is obtained as a colorless oil.

IR (CHCl$_3$): 2960, 2930, 2203, 1730, 1650, 1245, 972 cm$^{-1}$.

The starting material for the title compound was prepared as follows:

4(a) 5,6-Dihydro-5-iodo-15-methylprostacyclin Methyl Ester

Under agitation at 0° C. 33 ml. of a 2.5% ethereal iodine solution is added dropwise within 3 hours to a mixture of 1.1 g. of 15-methylprostaglandin-F$_{2\alpha}$ methyl ester, 2.70 g. of sodium bicarbonate, 30 ml. of ether, and 50 ml. of water. After 23 hours at 0° C., the mixture is diluted with ether, shaken with sodium thiosulfate solution, washed with water until neutral, dried over magnesium sulfate, and evaporated under vacuum. Filtration over silica gel with ether/ethyl acetate (1+1) yields 1.35 g. of the title compound as an oil.

IR (CHCl$_3$): 3600, 3400, 1730, 976 cm$^{-1}$.

4(b) 5,6-Dihydro-5-iodo-15-methylprostacyclin Methyl Ester 11,15-Diacetate 1.30 g. of the compound prepared according to Example 4(a) is dissolved in 12 ml. of pyridine and 3 ml. of acetic anhydride; then 100 mg. of 4-dimethylaminopyridine is added thereto, and the mixture is allowed to stand for 16 hours at 25° C. Thereafter the mixture is evaporated under vacuum and the residue filtered over silica gel with pentane/ether (8+2), thus obtaining 1.41 g. of the title compound as a colorless oil.

IR (CHCl$_3$): 2960, 2860, 1733, 1245, 976 cm$^{-1}$.

4(c) 15-Methylprostacyclin Methyl Ester 11,15-Diacetate

A mixture of 600 mg. of the diacetate prepared according to 4(b), 6 ml. of benzene, and 3 ml. of DBN is agitated for 20 hours at 45° C. under argon. The mixture is then diluted with ether, shaken three times with ice water, dried over sodium sulfate, and concentrated under vacuum at 20° C. The oily title compound is obtained which is used without further purification.

EXAMPLE 5

5-Cyano-15-methylprostacyclin.

A solution of 100 mg. of the compound prepared according to Example 4 in 6 ml. of methanol is combined with 1 ml. of 2 N sodium hydroxide solution and agitated for 5 hours at 25° C. under argon. The mixture is then concentrated under vacuum, taken up in 5 ml. of brine, adjusted to pH 7 with 0.5% citric acid, and extracted four times with methylene chloride. The organic extract is shaken once with brine, dried over magnesium sulfate, and evaporated under vacuum. The crude product is purified by filtration over silica gel with methylene chloride/isopropanol (85+15), thus obtaining 56 mg. of the title compound as a colorless oil.

IR (CHCl$_3$): 3600, 3300, 2930, 2862, 2210, 1712, 1650, 974 cm$^{-1}$.

EXAMPLE 6

5-Cyano-16,16-dimethylprostacyclin Methyl Ester 11,15-Diacetate

At −70° C. 3.5 ml. of a chlorosulfonyl isocyanate solution (production: Example 1) is added dropwise to a solution of 320 mg. of 16,16-dimethylprostacyclin methyl ester 11,15-diacetate in 4.5 ml. of ether; the mixture is gradually heated to 0° C. and 3.5 ml. of a solution of triethylamine (production: Example 1) is added dropwise thereto. The mixture is stirred for 1 hour at 0° C., for 15 mintes at 20° C., poured on ice-cold sodium bicarbonate solution, extracted three times with ether, the organic extract is shaken twice with brine, dried over magnesium sulfate, and evaporated under vacuum. Purification by PTLC (ether) yields 72 mg. of the title compound as a colorless oil.

IR (CHCl$_3$): 2960, 2930, 2204, 1732, 1650, 1245, 972 cm$^{-1}$.

The starting material for the title compound was prepared as follows:

6(a) 5,6-Dihydro-16,16-dimethyl-5-iodoprostacyclin Methyl Ester

Analogously to Example 1(a), 1.2 g. of 16,16-dimethylprostaglandin F$_{2\alpha}$ methyl ester yields 1.5 g. of the title compound as an oil.

IR (CHCl$_3$): 3600, 3400, 1730, 975 cm$^{-1}$.

6(b) 5,6-Dihydro-16,16-dimethyl-5-iodoprostacyclin Methyl Ester 11,15-Diacetate A solution of 820 mg. of the diol prepared according to Example 6(a) in 6 ml. of pyridine and 1.5 ml. of acetic anhydride is allowed to stand for 18 hours at room temperature, then evaporated under vacuum, and the residue is filtered with pentane/ether (1+1) over silica gel, thus obtaining 890 mg. of the title compound as a colorless oil.

IR (CHCl$_3$): 2960, 2948, 1732, 1245, 975 cm$^{-1}$.

6(c) 16,16-Dimethylprostacyclin Methyl Ester 11,15-Diacetate

Analogously to Example 1(c), 800 mg. of the diacetate prepared according to Example 6(b) and 4 ml. of DBN yield the title compound in the form of an oil.

EXAMPLE 7

5-Cyano-16,16-dimethylprostacyclin

A solution of 400 mg. of the compound prepared according to Example 6 in 25 ml. of methanol is combined with 4 ml. of 2 N sodium hydroxide solution and agitated for 6 hours at 25° C. under argon. Subsequently the mixture is concentrated under vacuum, taken up in 15 ml. of brine, adjusted to pH 7 with 1% citric acid, and extracted four times with methylene chloride. The organic extract is shaken once with brine, dried over magnesium sulfate, and evaporated under vacuum. The crude product is purified by filtration over silica gel (methylene chloride/isopropanol 85+15), thus obtaining 240 mg. of the title compound as a colorless oil.

IR (CHCl$_3$): 3600, 3300, 2930, 2860, 2210, 1710, 1650, 975 cm$^{-1}$.

EXAMPLE 8

5-Cyano-16-methylprostacyclin Methyl Ester 11,15-Diacetate

At −70° C. 14.4 ml. of a chlorosulfonyl isocyanate solution (production: 2.3 ml. of chlorosulfonyl isocyanate is dissolved in 50 ml. of absolute ether) is added dropwise to a solution of 1.30 g. of 16-methylprostacyclin methyl ester 11,15-diacetate in 18ml. of absolute ether. The mixture is gradually heated to 0° C. within 30 minutes and then 14.4 ml. of a solution of triethylamine (production: 400 mg. of triethylamine in 20 ml. of methylene chloride) is added dropwise thereto. The mixture is stirred for one hour at 0° C., for 15 minutes at 20° C., and pored on ice-cold sodium bicarbonate solution. The mixture is extracted three times with ether, the organic extract is shaken twice with brine, dried over magnesium sulfate, and evaporated under vacuum. Purification by PTLC (ether) yields 290 mg. of the title compound as a colorless oil.

IR ($CHCl_3$): 2960, 2932, 2203, 1730, 1650, 1250, 972 $cm^{-1}$.

The starting material for the title compound was produced as follows:

8(a) 5,6-Dihydro-5-iodo-16-methylprostacyclin Methyl Ester

Analogously to Example 1(a), 4.30 g. of 16-methylprostaglandin $F_{2\alpha}$ methyl ester yields 5.60 g. of the title compound as a colorless oil.

IR ($CHCl_3$): 3600, 3400, 2930, 1732, 975 $cm^{-1}$.

8(b) 5,6-Dihydro-5-iodo-16-methylprostacyclin Methyl Ester 11,15-Diacetate 5.51 g. of the compound prepared according to Example 8(a) is dissolved in 30 ml. of pyridine and 8 ml. of acetic anhydride, and the mixture is allowed to stand for 18 hours at 25° C. After evaporation under vacuum and filtration over silica gel (pentane/ether 7+3), 6 g. of the title compound is obtained as a colorless oil.

IR ($CHCl_3$): 2960, 2950, 2860, 1730, 1245, 975 $cm^{-1}$.

8(c) 16-Methylprostacyclin Methyl Ester 11,15-Diacetate

A mixture of 3 g. of the compound prepared according to Example 8(b), 30 ml. of benzene, and 15 ml. of DBN is agitated for 20 hours at 45° C. under argon, diluted with ether, shaken four times with ice water, dried over sodium sulfate, and concentrated under vacuum at 20° C., thus obtaining the oily title compound which is used without further purification.

EXAMPLE 9

5-Cyano-16-methylprostacyclin

A solution of 1 g. of the compound prepared in accordance with Example 8 in 50 ml. of methanol is combined with 10 ml. of 2N sodium hydroxide solution and agitated for 7 hours at 25° C. under argon. The mixture is then concentrated under vacuum, taken up in 50 ml. of brine, adjusted to pH 7 with 1% citric acid, and extracted four times with methylene chloride. The organic extract is shaken once with brine, dried over magnesium sulfate, and evaporated under vacuum. Filtration of the crude product over silica gel yields, with methylene chloride/isopropanol (85+15), 590 mg. of the title compound as a colorless oil.

IR ($CHCl_3$): 3600, 3300, 2933, 2860, 2210, 1710, 1650, 976 $cm^{-1}$.

EXAMPLE 10

5-Cyano-16-phenyl-17,18,19,20-tetranorprostacyclin Methyl Ester 11,15-Diacetate

At −70° C. 3.4 ml. of a chlorosulfonyl isocyanate solution (production see Example 1) is added dropwise to a solution of 300 mg. of 16-phenyl-17,18,19,20-tetranorprostacyclin methyl ester 11,15-diacetate in 4 ml. of ether. The mixture is heated within 30 minutes to 0° C. and then 3.4 ml. of a triethylamine solution in methylene chloride (production see Example 1) is added dropwise thereto. The mixture is agitated for one hour at 0° C., for 15 minutes at 20° C., then poured on ice-cold sodium bicarbonate solution, extracted with ether, the extract washed neutral with brine, dried over magnesium sulfate, and evaporated under vacuum. Purification by PTLC (ether) yields 80 mg. of the title compound as an oil.

IR ($CHCl_3$): 2960, 2205, 1733, 1651, 1602, 1245, 974 $cm^{-1}$.

The starting material for the above title compound was produced as follows:

10(a) 5,6-Dihydro-5-iodo-16-phenyl-17,18,19,20-tetranorprostacyclin Methyl Ester Analogously to Example 1(a), 1.05 g. of 16-phenyl-17,18,19,20-tetranorprostaglandin $F_{2\alpha}$ methyl ester yields 1.38 g. of the title compound as a colorless oil.

IR ($CHCl_3$): 3600, 3410, 1732, 1602, 975 $cm^{-1}$.

10(b) 5,6-Dihydro-5-iodo-16-phenyl-17,18,19,20-tetranorprostacyclin Methyl Ester 11,15-Diacetate A solution of 1.20 g. of the diol prepared according to Example 10(a) in 9 ml. of pyridine and 2.4 ml. of acetic anhydride is allowed to stand for 18 hours at room temperature. The mixture is then evaporated under vacuum, and the residue is filtered with pentane/ether (1+1) over silica gel, thus obtaining 1.31 g. of the title compound as a colorless oil.

IR ($CHCl_3$): 2958, 2950, 1732, 1602, 1245, 976 $cm^{-1}$.

10(c) 16-Phenyl-17,18,19,20-tetranorprostacyclin Methyl Ester 11,15-Diacetate

Analogously to Example 1(c), 1.25 g. of the diacetate produced according to Example 10(b) and 6 ml. of DBN yield the oily title compound which is further utilized in the form of the crude product.

EXAMPLE 11

5-Cyano-16-phenyl-17,18,19,20-tetranorprostacyclin

A solution of 610 mg. of the compound prepared in accordance with Example 10 in 28 ml. of methanol is combined with 6 ml. of 2N sodium hydroxide solution and agitated for 6 hours at 25° C. under argon. The mixture is then concentrated under vacuum, taken up in 15 ml. of brine, adjusted to pH 7 with 1% citric acid solution, and extracted four times with methylene chloride. The organic extract is shaken once with brine, dried over magnesium sulfate, and evaporated under vacuum. Purification of the crude product by filtration over silica gel (methylene chloride/isopropanol 9+1) yields 390 mg. of the title compound as a colorless oil.

IR ($CHCl_3$): 3600, 3310, 2930, 2860, 2212, 1712, 1650, 1602, 976 $cm^{-1}$.

EXAMPLE 12

5-Cyano-13,14-dihydro-16-methylprostacyclin Methyl Ester 11,15-Diacetate

At −70° C. 13 ml. of a chlorosulfonyl isocyanate solution (production see Example 1) is added dropwise to a solution of 1.15 g. of 13,14-dihydro-16-methylprostacyclin methyl ester 11,15-diacetate in 15 ml. of absolute ether. The mixture is heated within 30 minutes to 0° C., then 13 ml. of a solution of triethylamine in methylene chloride (see Example 1) is added dropwise thereto, the mixture is stirred for 1 hour at 0° C., poured on ice-cold sodium bicarbonate solution, and extracted with ether. The extract is washed with brine, dried over magnesium sulfate, and evaporated under vacuum at 25° C. With the aid of PTLC (ether), 300 mg. of the title compound is obtained as a colorless oil.

IR (CHCl$_3$): 2960, 2932, 2203, 1730, 1650, 1250 cm$^{-1}$.

The starting material for the title compound was prepared as follows:

12(a)

5,6-Dihydro-13,14-dihydro-5-iodo-16-methylprostacyclin Methyl Ester

Analogously to Example 1(a), 2.1 g. of 13,14-dihydro-16-methylprostaglandin F$_{2\alpha}$ methyl ester yields 2.6 g. of the title compound as a colorless oil.

IR (CHCl$_3$): 3600, 3400, 2930, 1730 cm$^{-1}$.

12(b)

5,6-Dihydro-13,14-dihydro-5-iodo-16-methylprostacyclin Methyl Ester 11,15-Diacetate Analogously to Example 1(b), 2.50 g. of the diol prepared according to Example 12(a) yields, after chromatography, 2.70 g. of the title compound as an oil.

IR (CHCl$_3$): 2958, 2950, 2855, 1732, 1245 cm$^{-1}$.

12(c) 13,14-Dihydro-16-methylprostacyclin Methyl Ester 11,15-Diacetate

Analogously to Example 1(c), 2 g. of the compound prepared according to Example 12(b) and 10 ml. of DBN yield the title compound, which is further used as the crude product.

EXAMPLE 13

5-Cyano-13,14-dihydro-16-methylprostacyclin

Analogously to Example 5, 250 mg. of the compound produced according to Example 12 and 2.5 ml. of 2N sodium hydroxide solution in 5 ml. of methanol yield 145 mg. of the title compound as a colorless oil.

IR (CHCl$_3$): 3600, 3300, 2930, 2862, 2212, 1710 cm$^{-1}$.

EXAMPLE 14

5-Cyano-N-methanesulfonylprostacyclin Carboxamide 377 mg. of 5-cyanoprostacyclin (production see Example 3), 3 ml. of pyridine, and 1 ml. of acetic anhydride are allowed to stand for 16 hours at room temperature and then evaporated under vacuum. The residue is dissolved in 10 ml. of absolute acetonitrile, 120 mg. of triethylamine is added thereto, and the mixture is combined with a solution of 150 mg. of methylsulfonyl isocyanate in 8 ml. of acetonitrile. The mixture is stirred for 4 hours at 20° C., concentrated under vacuum, combined with 10 ml. of water, adjusted to pH 7 with 1% citric acid solution, and extracted with ether. The organic extract is shaken with brine, dried over magnesium sulfate, and evaporated under vacuum. Purification by PTLC (ether) yields 340 mg. of the methanesulfonyl carboxamide. To split off the acetate blocking groups, the product is dissolved in 10 ml. of methanol, combined with 240 mg. of potassium carbonate, and agitated for 3 hours at 20° C. under argon. The mixture is then diluted with brine, adjusted to pH 7 with 1% citric acid solution, extracted with methylene chloride, the extract shaken with brine, dried over magnesium sulfate, and evaporated under vacuum.

Filtration over silica gel with methylene chloride/isopropanol (9+1) yields 203 mg. of the title compound as a colorless oil.

IR (CHCl$_3$): 3400, 2935, 2865, 2211, 1720, 1650, 1340, 975 cm$^{-1}$.

EXAMPLE 15

5-Cyano-16-methyl-N-methanesulfonylprostacyclin Carboxamide

Analogously to Example 14, 250 mg. of 5-cyano-16-methylprostacyclin yields 173 mg. of the title compound as an oil.

IR (CHCl$_3$): 3400, 2940, 2865, 2210, 1718, 1650, 972 cm$^{-1}$.

EXAMPLE 16

5-Cyano-N-acetylprostacyclin Carboxamide 190 mg. of 5-cyanoprostacyclin (see Example 3), 1.5 ml. of pyridine, and 0.5 ml. of acetic anhydride are allowed to stand for 16 hours at room temperature and then evaporated under vacuum. The residue is dissolved in 6 ml. of acetonitrile, a solution of 75 mg. of triethylamine in 6 ml. of acetonitrile is added thereto, and the mixture is combined at 0° C. with a solution of 55 mg. of acetyl isocyanate in 6 ml. of acetonitrile. The mixture is stirred for 2 hours at 20° C., concentrated under vacuum, combined with 10 ml. of water, adjusted to pH 7 with 1% citric acid solution, and extracted with ether. The extract is shaken with brine, dried over magnesium sulfate, and evaporated under vacuum. Purification by PTLC (ether/pentane 7+3) yields 160 mg. of the acetyl carboxamide. To split off the acetate blocking groups, the product is dissolved in 5 ml. of methanol, combined with 105 mg. of potassium carbonate, and agitated for 3 hours at 20° C. under argon. The mixture is then diluted with brine, adjusted to pH 7 with 1% citric acid solution, the extract shaken with brine, dried over magnesium sulfate, and evaporated under vacuum. Filtration over silica gel (methylene chloride/isopropanol 9+1) yields 105 mg. of the title compound as an oil.

IR (CHCl$_3$): 3600, 3400, 2960, 2210, 1733, 1705, 1650, 973 cm$^{-1}$.

EXAMPLE 17

5-Cyano-15-methyl-N-acetylprostacyclin Carboxamide

Analogously to Example 16, 225 mg. of 5-cyano-15-methylprostacyclin (Example 5) yields 152 mg. of the title compound as an oil.

IR (CHCl$_3$): 3600, 3400, 2955, 2212, 1733, 1706, 1650, 973 cm$^{-1}$.

EXAMPLE 18

5-Cyano-16,16-dimethyl-N-acetylprostacyclin Carboxamide

Analogously to Example 16, 170 mg. of 5-cyano-16,16-dimethylprostacyclin (Example 7) yields 95 mg. of the title compound as an oil.

IR (CHCl$_3$): 3600, 3410, 2960, 2210, 1732, 1705, 1650, 976 cm$^{-1}$.

EXAMPLE 19

5-Cyano-16-methyl-N-acetylprostacyclin Carboxamide

Analogously to Example 16, 152 mg. of 5-cyano-16-methylprostacyclin (Example 9) yields 102 mg. of the title compound as an oil.

IR (CHCl₃): 3600, 3410, 2955, 2210, 1735, 1708, 1650, 974 cm⁻¹.

EXAMPLE 20

5-Cyano-N-acetyl-16-phenyl-17,18,19,20-tetranorprostacyclin Carboxamide

Analogously to Example 1(b), 165 mg. of 5-cyano-16-phenyl-17,18,19,20-tetranorprostacyclin yields 100 mg. of the title compound as a colorless oil.

IR (CHCl₃): 3600, 3400, 2945, 2212, 1734, 1708, 1650, 1602, 975 cm⁻¹.

EXAMPLE 21

5-Cyano-13,14-dihydro-16-methyl-N-acetylprostacyclin Carboxamide

Analogously to Example 16, 95 mg. of 5-cyano-13,14-dihydro-16-methylprostacyclin yields 57 mg. of the title compound as an oil.

IR (CHCl₃): 3600, 3400, 2955, 2210, 1734, 1706, 1650 cm⁻¹.

EXAMPLE 22

Tris(hydroxymethyl)aminomethane Salt of 5-Cyanoprostacyclin

At 80° C. a solution of 60 mg. of tris(hydroxymethyl)aminomethane in 0.2 ml. of water is added under agitation to a solution of 190 mg. of 5-cyanoprostacyclin in 7 ml. of acetonitrile. The mixture is stirred for 16 hours at room temperature. After separation of the solvent, 185 mg. of the title compound is obtained.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostane derivative of the formula

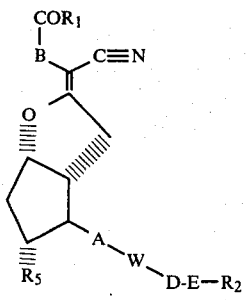

wherein
R₁ is (a) OR₃, wherein R₃ is hydrogen, C₁₋₁₀ alkyl, C₄₋cycloalkyl, C₆₋₁₀ aryl, or an aromatic heteromonocycle containing 5 or 6 ring atoms of which only one is a hetero atom of O, N or S; or (b) NHR₄, wherein R₄ is the acyl group of a C₁₋₁₅ hydrocarbon carboxylic or sulfonic acid;
B is straight-chain or branched alkylene of 2–10 carbon atoms;
A is —CH₂—CH₂—, cis—CH=CH—, trans—CH=CH— or C≡C—;

W is

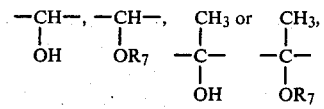

wherein OH and OR₇ are in the α- or β-position and wherein R₇ is an acyl group of a C₁₋₁₅ hydrocarbon carboxylic or sulfonic acid; or tetrahydropyranyl, tetrahydrofuranyl, α-ethoxyethyl, trimethylsilyl, dimethyl-tert-butylsilyl or tribenzylsilyl;
D and E together are a direct bond; or
D is straight-chain or branched alkylene of 1–5 carbon atoms; and
E is oxygen, sulfur or a direct bond;
R₂ is C₁₋₁₀ alkyl, C₁₋₁₀ alkenyl, C₁₋₁₀ alkynyl, C₄₋cycloalkyl, C₆₋₁₀ aryl or an aromatic heteromonocycle containing 5 or 6 ring atoms of which only one is a hetero atom of O, N or S;
R₅ is OH or OR₇; and
for the compounds wherein R₃ is H, a salt thereof with a physiologically compatible base.

2. 5-Cyanoprostacyclin methyl ester 11,15-diacetate, a compound of claim 1.

3. 5-Cyanoprostacyclin methyl ester, a compound of claim 1.

4. 5-Cyanoprostacyclin, a compound of claim 1.

5. 5-Cyano-15-methylprostacyclin methyl ester 11,15-diacetate, a compound of claim 1.

6. 5-Cyano-15-methylprostacyclin, a compound of claim 1.

7. 5-Cyano-16,16-dimethylprostacyclin methyl ester 11,15-diacetate, a compound of claim 1.

8. 5-Cyano-16,16-dimethylprostacyclin, a compound of claim 1.

9. 5-Cyano-16-methylprostacyclin methyl ester 11,15-diacetate, a compound of claim 1.

10. 5-Cyano-16-methylprostacyclin, a compound of claim 1.

11. 5-Cyano-16-phenyl-17,18,19,20-tetranorprostacyclin methyl ester 11,15-diacetate, a compound of claim 1.

12. 5-Cyano-16-phenyl-17,18,19,20-tetranorprostacyclin, a compound of claim 1.

13. 5-Cyano-13,14-dihydro-16-methylprostacyclin methyl ester 11,15-diacetate, a compound of claim 1.

14. 5-Cyano-13,14-dihydro-16-methylprostacyclin, a compound of claim 1.

15. 5-Cyano-N-methanesulfonylprostacyclin carboxamide, a compound of claim 1.

16. 5-Cyano-16-methyl-N-methanesulfonylprostacyclin carboxamide, a compound of claim 1.

17. 5-Cyano-N-actylprostacyclin carboxamide, a compound of claim 1.

18. 5-Cyano-15-methyl-N-acetylprostacyclin carboxamide, a compound of claim 1.

19. 5-Cyano-16,16-dimethyl-N-acetylprostacyclin carboxamide, a compound of claim 1.

20. 5-Cyano-16-methyl-N-acetylprostacyclin carboxamide, a compound of claim 1.

21. 5-Cyano-N-acetyl-16-phenyl-17,18,19,20-tetranorprostacyclin carboxamide, a compound of claim 1.

22. 5-Cyano-13,14-dihydro-16-methyl-N-acetylprostacyclin carboxamide, a compound of claim 1.

23. Tris(hydroxymethyl)aminomethane salt of 5-cyanoprostacyclin, a compound of claim 1.

24. A pharmaceutical composition comprising an amount of a compound of claim 1 effective to lower blood pressure and a pharmaceutically acceptable carrier.

25. A method of lowering blood pressure in mammals which comprises administering an amount of a compound of claim 1 effective to lower blood pressure.

26. A stabilized prostacyclin having a —C≡N group in the 5-position.

27. A method of stabilizing a prostacyclin which comprises introducing a —C≡N group in the 5-position thereof, thereby stabilizing the prostacyclin.

* * * * *

UNITED STATES PATENT AND TRADEMARK OFFICE
CERTIFICATE OF CORRECTION

PATENT NO. : 4,219,479
DATED : August 26, 1980
INVENTOR(S) : Helmut Vorbruggen et al It is certified that error appears in the above-identified patent and that said Letters Patent are hereby corrected as shown below:

Column 17, line 60: reads " $C_{4-}$ cycloalkyl, $C_{6-10}$ aryl, or an aromatic "

should read -- $C_{4-14}$ cycloalkyl, $C_{6-10}$ aryl, or an aromatic -- .

Column 18, line 19: reads " $R_2$ is $C_{1-10}$ arkyl, $C_{1-10}$ alkenyl, $C_{1-10}$ alkynyl, $C_{4-}$cy- "

should read -- $R_2$ is $C_{1-10}$ alkyl, $C_{1-10}$ alkenyl, $C_{1-10}$ alkynyl, $C_{4-14}$ cy -- .

Signed and Sealed this

Tenth Day of February 1981

[SEAL]

Attest:

RENE D. TEGTMEYER

Attesting Officer

Acting Commissioner of Patents and Trademarks